United States Patent

Uemura et al.

Patent Number: 5,099,853
Date of Patent: Mar. 31, 1992

[54] BLOOD PRESSURE MONITORING SYSTEM

[75] Inventors: Masahiro Uemura, Komaki; Hideichi Tsuda, Kasugai; Hifumi Yokoe, Nagoya, all of Japan

[73] Assignee: Colin Electronics Co., Ltd., Aichi, Japan

[21] Appl. No.: 204,555

[22] PCT Filed: Dec. 25, 1987

[86] PCT No.: PCT/JP87/01033

§ 371 Date: May 2, 1988

§ 102(e) Date: May 2, 1988

[87] PCT Pub. No.: WO88/04910

PCT Pub. Date: Jul. 14, 1988

[30] Foreign Application Priority Data

Dec. 25, 1986 [JP] Japan .................................. 61-311569

[51] Int. Cl.$^5$ ................................................ A61B 5/02
[52] U.S. Cl. ...................................... 128/679; 128/681
[58] Field of Search ............................ 128/672, 677-690

[56] References Cited

U.S. PATENT DOCUMENTS

| 4,423,738 | 1/1984 | Newgard | 128/672 |
| 4,669,485 | 6/1987 | Russell | 128/677 X |
| 4,699,152 | 10/1987 | Link | 128/677 X |
| 4,799,491 | 1/1989 | Eckerle | 128/672 |

FOREIGN PATENT DOCUMENTS 0188894  7/1986  European Pat. Off.

OTHER PUBLICATIONS

"Idea to measure diastolic arterial pressure by volume oscillometric method in human fingers", Medical and Biological Engineering and Computing, vol. 24, No. 5, Sep. 1986, PP. 549-554.

"Analysis for the non—invasive determination of arterial properties and for the transoutaneous continuous monitoring of arterial blood pressure", Medical and Biological Engineering and Computing, vol. 16, No. 6, Nov. 1978, pp. 715-726.

Primary Examiner—Lee S. Cohen
Assistant Examiner—John P. Lacyk
Attorney, Agent, or Firm—Oliff & Berridge

[57] ABSTRACT

It is desirable to minimize discomfort of a living body due to pressing by a blood pressure monitoring system of a type which monitors the blood pressure of the living body for a long period of time. The present invention is constituted by including pulse wave detecting device for detecting pulse waves of an arterial vessel of a living body, blood pressure measuring device for measuring an actual blood pressure of the living body, and control device for determining a relationship between the pulse waves detected by the pulse wave detecting device and the actual blood pressure measured by the blood pressure measuring device, determining blood pressures according to the thus-determined relationship and based on the pulse waves, and commanding a display to continuously display the thus-determined blood pressures thereon. In accordance with the present invention, blood pressures are determined according to the relationship between the actual blood pressure and the pulse waves, which is determined by the control device, and based on the pulse waves, and the thus determined blood pressures are continuously displayed, thereby eliminating the operation of successively obtaining measurements of the actual blood pressure by using a cuff, for example, and minimizing discomfort felt by the living body.

18 Claims, 8 Drawing Sheets

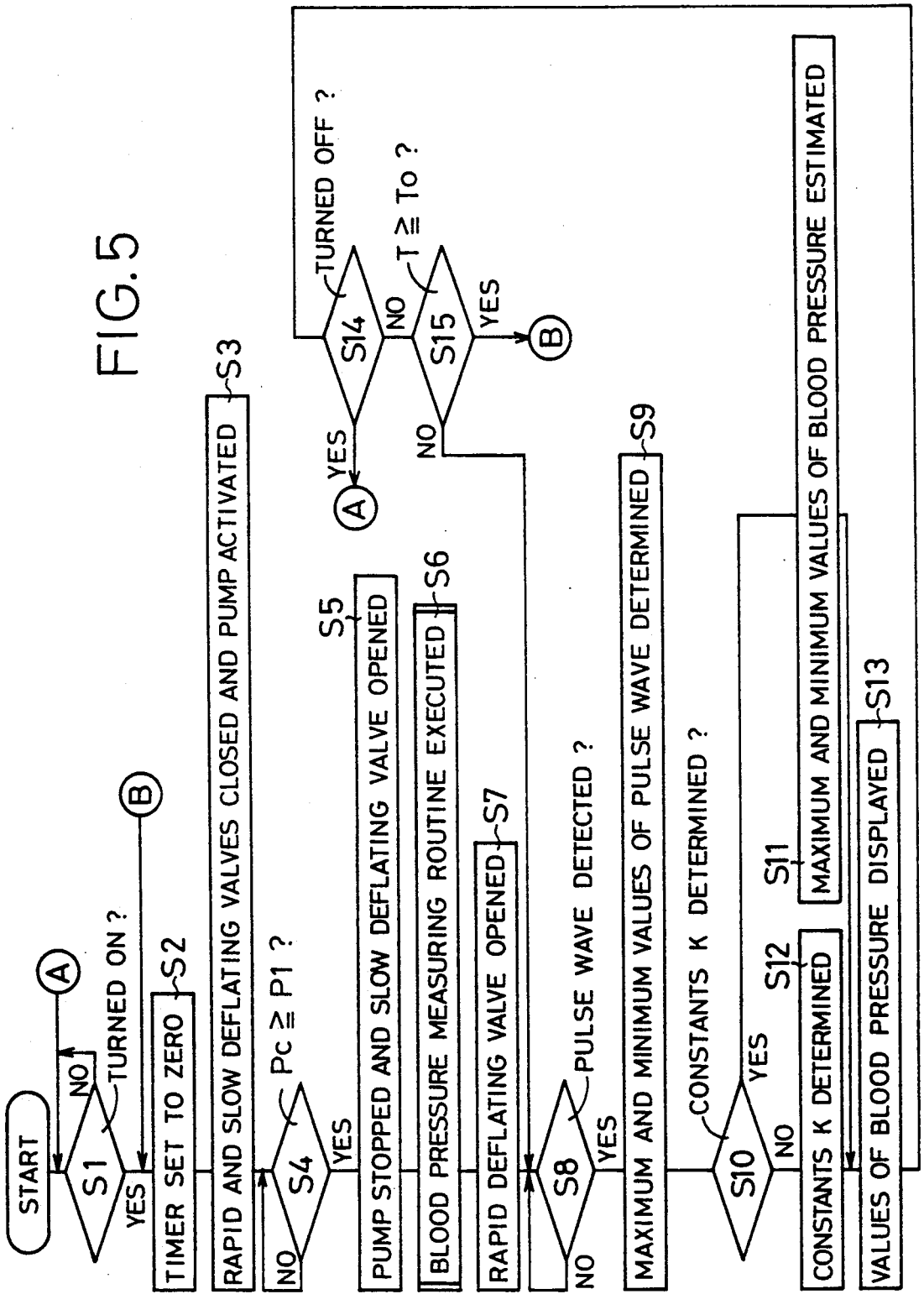

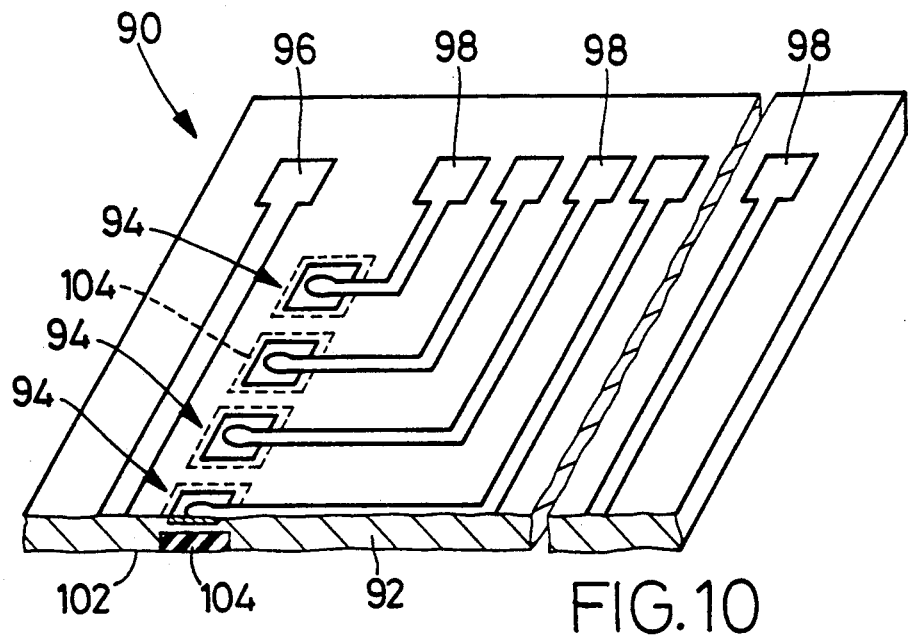
FIG. 10
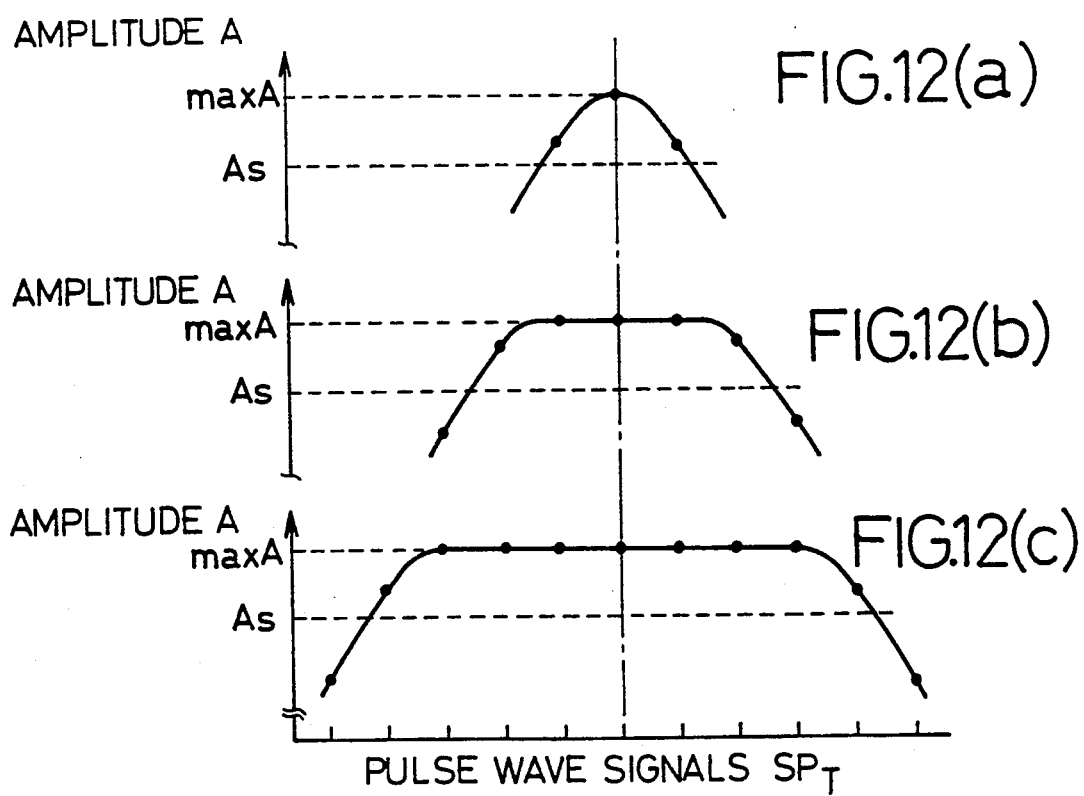
FIG.12(a)
FIG.12(b)
FIG.12(c)

BLOOD PRESSURE MONITORING SYSTEM

FIELD OF THE INVENTION

The present invention relates to a blood pressure monitoring system for continuously monitoring blood pressures which are determined based on the pulse waves produced by pressing a portion of a living body.

BACKGROUND OF THE INVENTION

It is a widely-employed method for measuring blood pressure of a living body to press a portion of the living body by a cuff, etc. to detect pressure oscillation waves (pulse waves) produced in synchronization with heartbeats of the living body and determine values of blood pressure of the living body based on a change in magnitude of the detected pressure oscillation waves.

However, the above-indicated blood pressure measuring method is not recommendable for application to such a living body, for example a patient after a surgical operation, whose blood pressure must be continuously monitored during a comparatively long period of time, because a portion of the living body is successively pressed during the period, thereby giving appreciable discomfort to the living body.

DISCLOSURE OF THE INVENTION

The present invention has been developed in the background indicated above, and the gist thereof resides in providing a blood pressure monitoring system of a type for continuously displaying blood pressure of a living body on a display to monitor the blood pressure of the living body, the system including (a) pulse wave detecting means for detecting pulse waves of an arterial vessel of the living body; (b) blood pressure measuring means for measuring an actual blood pressure of the living body; and (c) control means for determining a relationship between the pulse waves detected by the pulse wave detecting means and the actual blood pressure measured by the blood pressure measuring means, determining blood pressures according to the thus-determined relationship and based on the pulse waves, and commanding the display to successively display the thus-determined blood pressures thereon.

As shown in the view of FIG. 1 corresponding to claim, at the time the blood pressure measuring means measures an actual blood pressure, the control means determines a relationship between the measured actual blood pressure and the pulse waves of an arterial vessel which are continuously detected by the pulse wave detecting means, and a change in blood pressure is continuously displayed on the display according to the thus-determined relationship and based on the pulse waves.

Therefore, in the present invention, it is unnecessary to successively obtain measurements of the actual blood pressure of the living body to monitor his or her blood pressure, and a long-time continuous monitoring of the blood pressure may be conducted without successively pressing a portion of the living body. Thus, the living body being monitored is prevented from any obstruction of blood circulation and is not subjected to appreciable discomfort.

Since the pulse wave detecting means of the present invention is adapted to detect pulse waves of an arterial vessel, the pulse waves detected are almost free from influence of breathing of the living body. Therefore, accurate monitoring of blood pressure is conducted. Although it is possible to use a cuff wound around an arm of a living body as pulse wave detecting means to detect pressure oscillations of the cuff as pulse waves, the pulse waves detected represent variation in volume of arteries and veins, and the variation in volume is liable to be influenced by breathing.

BRIEF DESCRIPTION OF THE DRAWINGS

FIG. 5 is a view showing a flow chart used for the operation of the embodiment of FIG. 2.

FIG. 10 is a perspective view, partly in cross section, showing a plurality of pressure sensors provided on the device of FIG. 9.

FIG. 12 is a view of three graphs (a), (b) and (c) each showing amplitudes of the pulse wave signals generated by the pressure sensors in a direction perpendicular to the arterial vessel, the pressing forces employed in cases (a), (b) and (c) being different from each other.

BEST MODE FOR CARRYING OUT THE INVENTION

There will be described in detail one embodiment of the present invention with reference to the drawings.

Figure 2:
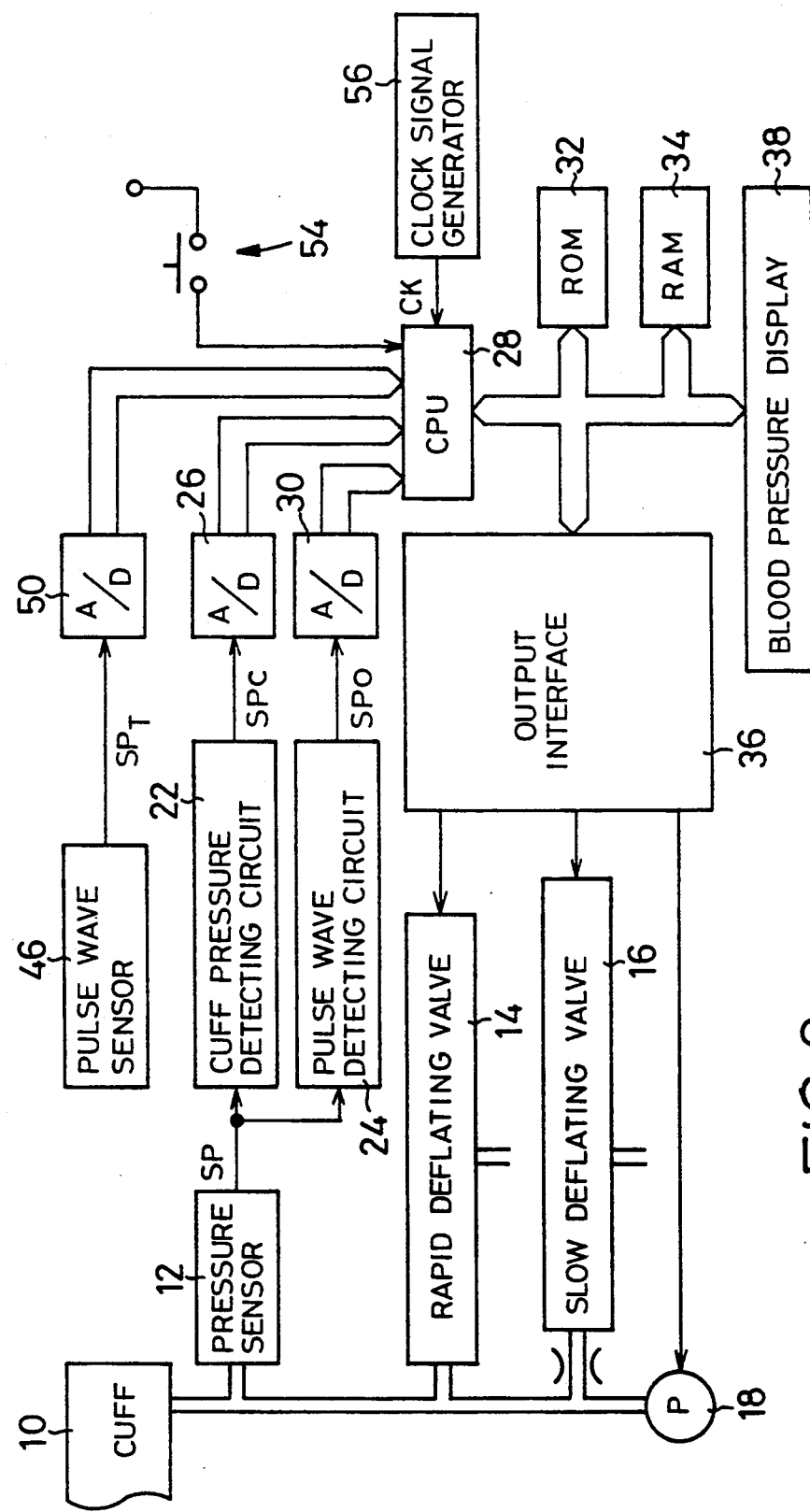
FIG. 2 is a diagrammatic view illustrating the arrangement of one embodiment of the present invention.

FIG. 2 is a view illustrating the arrangement of the present embodiment in the form of a blood pressure monitoring system. In the figure, there is shown a cuff 10 like a rubber bag which is wound around an upper arm, etc. of a living body or a subject to press the arm. A pressure sensor 12, a rapid deflating valve 14, a slow deflating valve 16, and a pressure supplying device in the form of an electrically operated pump 18 are connected through a tube 20 to the cuff 10. The pressure sensor 12 is adapted to detect a pressure in the cuff 10 and supply a pressure signal SP to both cuff pressure detect circuit 22 and pulse wave detect circuit 24. The cuff pressure detect circuit 22 includes low pass filler for discriminating a static pressure in the cuff 10 from the pressure signal SP, and is adapted to supply a cuff pressure signal SPc representative of the static pressure cuff pressure) Pc, to CPU 28 via A/D converter 26. The pulse wave detect circuit 24 includes band pass filter for discriminating from the pressure signal SP a dynamic pressure in the cuff 10, that is, a pressure-oscillation component (pulse waves) which is generated in synchronization with heartbeats, and is adapted to supply a pulse wave signal SPo representative of the pressure oscillation, to the CPU 28 via A/D converter 30.

Figure 1:
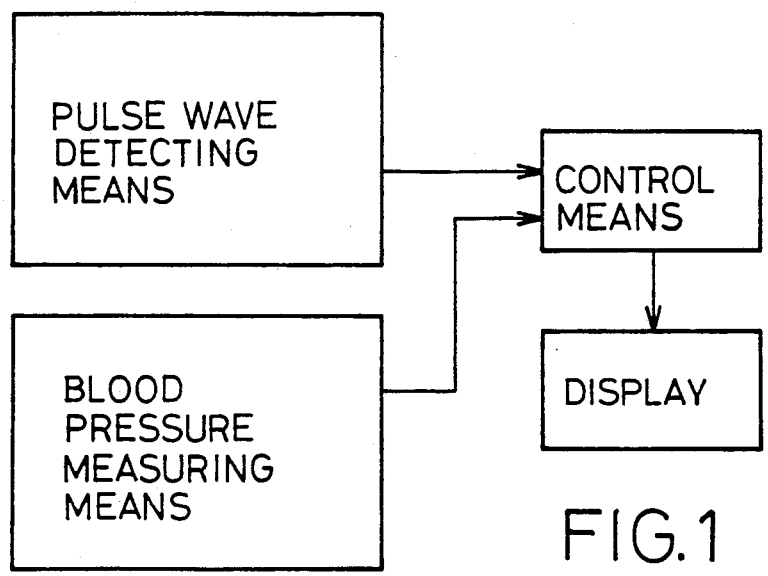
FIG. 1 is a view corresponding to claim of the present invention.
Figure 3:
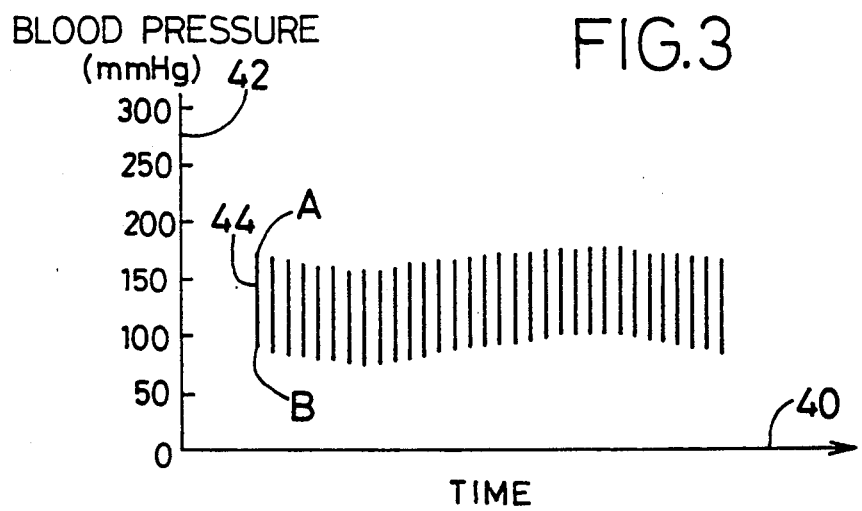
FIG. 3 is a view showing an example of a blood pressure trend displayed on a display of the embodiment of FIG. 2.

The CPU 28 is adapted to process input signals according to programs pre-stored in ROM 32 while utilizing storing function of RAM 34 to generate drive signals to the rapid deflating valve 14, slow deflating valve 16 and electrically operated pump 18, respectively, via output interface 36 and command a blood pressure display 38 to display values of blood pressure. The blood pressure display 38 indicates on a Braun tube thereof a two-dimensional table, as shown in FIG. 3, which table has a horizontal axis 40 indicative of time and a vertical axis 42 indicative of blood pressure (mmHg). The display 38 is adapted to timewise successively display, on the two-dimensional table, tars 44 according to display signals supplied from the CPU 28. The upper and lower ends A and B of each bar 44 are indicative of a maximum and a minimum value of blood pressure.

Figure 4:
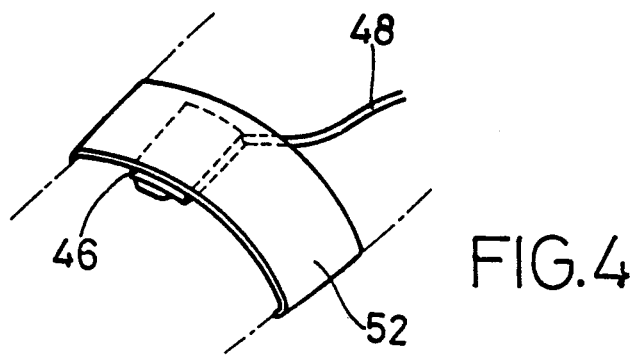
FIG. 4 is a view showing a pulse wave sensor of FIG. 2 when it is in pressed contact with a portion of a living body.

A pulse wave sensor 46 is connected to the CPU 28 via a cable 48 and A/D converter 50. As shown in FIG. 4, the pulse wave sensor 46 is attached to a band 52 having a pair of zippers (not shown) at the opposite ends of the band 52. The pulse wave sensor 46 is located above a radius of the living body in the vicinity of a wrist where pulse waves are easily gathered, and is locally pressed against an arterial vessel above the radius under a comparatively low constant pressure not more than about 20 mmHg, for example, by winding the band 52 around the wrist of the living body and zipping the pair of zippers of the band 52. The pulse wave sensor 46 is adapted to detect pulse waves of the arterial vessel above the radius and supply a pulse wave signal $SP_T$ indicative of the pulse waves, to the CPU 28 via A/D converter 50. As the pulse wave sensor 46, is used a semiconductor strain sensor or a piezoelectric element capable of converting a pulsation of an arterial vessel to an electric signal. An ON/OFF switch 54 is adapted to supply an ON/OFF signal to the CPU 28 upon depression thereof, and the system is turned on or off each time the ON/OFF switch 54 is operated by depression. A clock signal generator 56 is adapted to supply to the CPU 28 pulse signals CK having a predetermined frequency.

There will be described the operation of the present embodiment with reference to the flow chart of FIG. 5.

Upon operation of a power switch (not shown), step S1 is executed to check whether or not the ON/OFF switch 54 has been depressed, that is, whether or not ON/OFF signal is present at the CPU 28. After the ON/OFF switch 54 has been operated by depression with the cuff 10 wound around the upper arm, etc. of the living body, step S1 is followed by step S2 to clear counting T of timer to zero so that the timer thereafter re-starts counting the pulse signals CK supplied from the clock signal generator 56. Step S2 is followed by step S3 to close the rapid and slow deflating valves 14 and 16 and actuate the electrically operated pump 18. Consequently, the cuff pressure Pc is raised. Step S3 is followed by step S4 to check whether or not the cuff pressure Pc has reached a predetermined maximum pressure Pl. The maximum pressure Pl is predetermined to be above an estimated maximum blood pressure of the living body, for example about 180 mmHg. Where the cuff pressure Pc has reached the maximum pressure Pl, step S4 is followed by step S5.

Step S5 is provided to stop the electrically operated pump 18 and open the slow deflating valve 16 to slowly discharge air from the cuff 10 and thereby gradually lower the cuff pressure Pc. In this process, is executed a blood pressure measuring routine of step S6, which corresponds to blood pressure measuring means of the present embodiment. That is, a maximum blood pressure H (mmHg) and a minimum blood pressure L (mmHg) are determined based on the cuff pressure Pc and a variation in magnitude of the pulse waves, that is, pressure oscillations of the cuff 10 represented by the pulse wave signal SPo, and the thus-determined values H and L are stored in the RAM 34.

Figure 6:
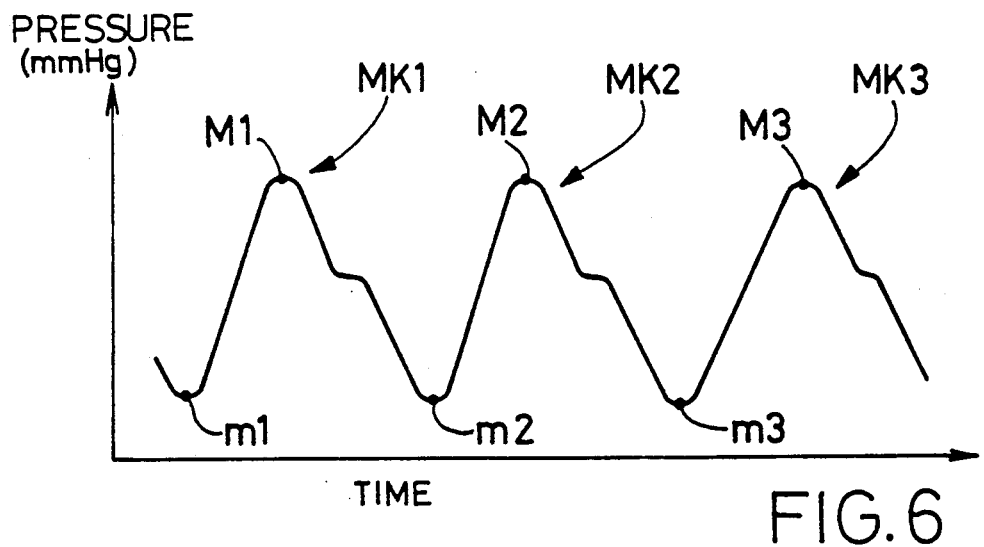
FIG. 6 is a view showing an example of pulse waves which are continuously detected in the embodiment of FIG. 1.

Upon completion of step S6, step S7 is implemented to open the rapid deflating valve 14 to rapidly discharge air from the cuff 10. Step S7 is followed by steps S8 and the following, in which, as shown in FIG. 6, successive pulse waves MK1, MK2, . . . are detected and stored, and a maximum blood pressure SYS and a minimum blood pressure DIA are successively determined based on magnitudes of the thus-stored pulse waves.

More specifically, step S8 is provided to check whether or not one pulse wave has been detected, based on a pulse wave signal $SP_T$ supplied from the pulse wave sensor 46. In the case where the first pulse wave MK1 has been detected, the first pulse wave MK1 detected is stored. Step S8 is followed by step S9 to determine a maximum value $M_1$ (mmHg) and a minimum value $m_1$ (mmHg) of the pulse wave MK1 based on the stored pulse wave. Step S9 is followed by step S10 to check whether or not have been determined a pair of constants Kmax and Kmin which are employed in the following equations (1) and (2) for determining a maximum and a minimum value SYS and DIA of blood pressure based on a maximum value Mmax (mmHg) and a minimum value Mmin (mmHg) of each pulse wave, respectively:

$$SYS = Kmax \cdot Mmax$$

$$DIA = Kmin \cdot Mmin$$

In the case where the constants Kmax and Kmin have been determined, step 10 is followed by step S11. However, since the first pulse wave MKI has been just detected and stored now and accordingly the constants Kmax and Kmin have not been determined yet, step S10 is followed by step S12.

Step S12 is provided to determine according the following equations (3) and (4) constants Kmax and Kmin based on the maximum and minimum blood pressure H and L stored in the RAM 34 at step S6 and the maximum and minimum values $M_1$ and $m_1$ of the first pulse wave MK1 determined at step S9:

$$Kmax = H/M_1$$

$$Kmin = L/m_1$$

Thus, a relationship between the radius pulse waves and the upper-arm blood pressure H and L is determined.

Step 12 is followed by step S13 to supply a display signal representative of the maximum and minimum blood pressure H and L to the blood pressure display 38, which upon receipt of the display signal displays on the Braun tube thereof the first bar 44 indicative of the blood pressure H and L. Subsequently, step S14 is implemented to check whether or not the ON/OFF switch 54 has been operated again. In the case where the switch 54 has been operated, the operation of the system is ended. However, since a sufficient trend of the blood pressure has not been obtained yet, normally the ON/OFF switch 54 has not been re-operated. Accordingly, step S14 is followed by step S15 to check whether or not the counting T of the timer has reached a predetermined value To. The value To corresponds to the time of a predetermined regular interval at which the correspondence relationship determined at step S12 is updated for correction, and is predetermined to be within the range of about 5 to 10 minutes. Accordingly, where the counting T has reached the value To, step S15 is followed by steps S2 and the following. However, since the first pulse wave MK1 has been just detected now after the operation of the instant system is started, the counting T has not reached the value To yet. Therefore, step S15 is followed by steps S8 and the following.

Where the second pulse wave MK2 following the first pulse wave MK1 in detected at step S8, step S8 is followed by step S9 to determine a maximum value $M_2$ (mmHg) and a minimum value $m_2$ (mmHg) of the second pulse wave MK2. Since the constants Kmax and Kmin have been determined at step S12, as previously described, the checking at step S10 following step S9 is formed to be affirmative. Accordingly, step S10 is followed by step Sll to determine according to the above-indicated equations (1) and (2) a maximum and a minimum blood pressure SYS and DIA corresponding to the maximum and minimum values $M_2$ and $m_2$ of the second pulse wave MK2. The thus-determined blood pressure SYS and DIA are estimated to be equal to actual blood pressure of the living body at the time of detection of the second pulse wave MK2. Step 13 is provided to display the thus-estimated blood pressure SYS and DIA on the Braun tube of the display 38. Therefore, steps Sll, S12 and S13 correspond to control means of the present embodiment.

Thereafter, the implementation of steps S8 through S15 is repeated until the checking at step S14 or step S15 is found to be affirmative. Each time a pulse wave is detected, that is, each time the arterial vessel is pulsated, a maximum and a minimum value of blood pressure is successively determined according to the correspondence-relationship equations (1) and (2) and based on the maximum and minimum values on the detected pulse wave, and successively displayed on the display 38.

When the counting T of the timer has reached the value To and accordingly the checking at step S15 is found to be affirmative, steps S2 and the following are implemented to obtain another measurement of maximum and minimum values H and L of the actual blood pressure at step S6, and determine maximum and minimum values of a leading pulse wave at step S8. Based on the another measurement of the actual blood pressure and the maximum and minimum values of the leading pulse wave, another pair of constants Kmax and Kmin for the correspondence-relationship equations (1) and (2) are determined. According to the newly-determined correspondence-relationship equations (1) and (2), the blood pressure is continuously determined based on maximum and minimum values of each of the pulse waves detected following the leading pulse wave, and the thus-determined values of the blood pressure are successively displayed.

In the present embodiment, while the maximum and minimum values of the actual blood pressure are periodically measured, the pulse waves are detected above the radius by pressing the pulse wave sensor 46 against the radial artery under a comparatively low pressure not more than about 20 mmHg. The correspondence relationship between the maximum and minimum values of the pulse waves and the maximum and minimum values of the actual blood pressure is periodically updated. The blood pressure is continuously determined according to the periodically-updated correspondence relationship and based on magnitudes of the pulse waves detected by the pulse wave sensor 46, and the thus-determined blood pressure is continuously displayed. Accordingly, in the present embodiment, for continuously monitoring the blood pressure, the living body has only to undergo pressing of a portion of the body which is conducted at regular intervals of about 5 to 10 minutes, for example, to periodically measure the actual blood pressure of the living body, as opposed to the conventional system which is adapted to always press a portion of a living body to continuously monitor the blood pressure of the living body. Therefore, a living body whose blood pressure is being monitored by the instant system is free from any obstruction on blood circulation even during a long-time continuous monitoring, and feels little discomfort.

Moreover, the present embodiment provides information of medical significance, that is, a maximum and a minimum blood pressure corresponding to each pulsation of an arterial vessel of the living body. Furthermore, in the present embodiment, since the pulse waves are detected by the pulse wave sensor 46 from the arterial vessel located above the radius, the detected pulse waves are almost free from influence of breathing of the living body, contributing to assuring accurate monitoring of the blood pressure. In this connection, it is noted that it is possible to use as the pulse wave detecting means a cuff wound around an upper arm of a living body and detect pressure oscillations of the cuff as pulse waves. In this case, however, the pulse waves detected are under influence of variation in volume of arteries and veins, which variation in volume is at to be influenced by breathing of the living body. Also, it is to be understood that the present embodiment may be adapted to continuously determine one of the maximum and minimum blood pressure, average blood pressure defined as the average value of the maximum and minimum blood pressure, or other sorts of blood pressure.

There will be described another embodiment of the present invention. It is noted that, in the following embodiments, the same parts thereof as those of the above described embodiment are designated by the same reference numerals, and descriptions about such parts are skipped.

Figure 7:
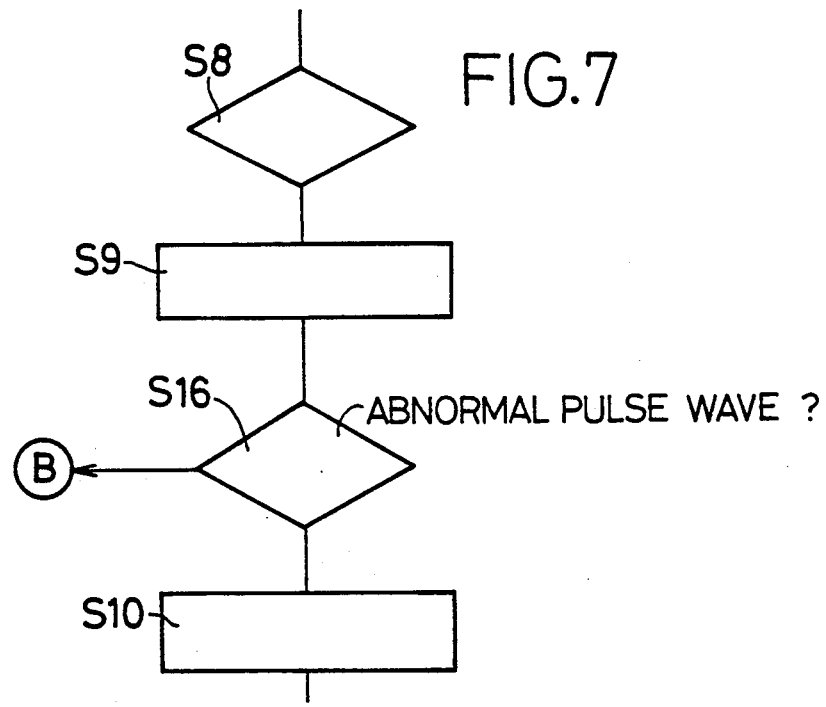
FIG. 7 is a view showing a main portion of a flow chart of another embodiment of the present invention.
Figure 8:
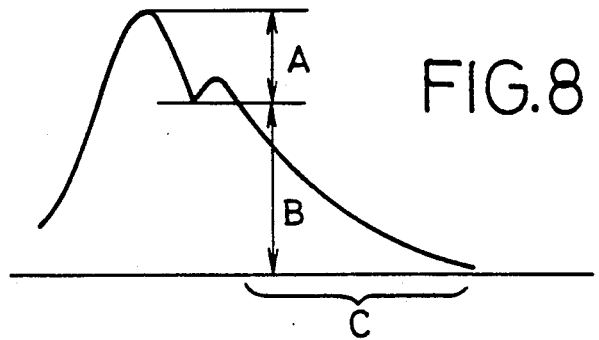
FIG. 8 is a view illustrating the location of a notch of a radius pulse wave or a portion of the pulse wave corresponding to the diastole of the heart.

As shown in FIG. 7, it is possible to add step S16, as abnormal pulse wave detecting means, for updating the relationship in the case where it is judged from the radius pulse waves that the blood pressure determined based on the pulse waves has been deflected from the upper arm blood pressure measured at step S6, for example in the case of a motion of the portion of the living body at which the pulse waves are detected or in the case of a change in resistance to peripheral blood flow. When the condition of the pressed pressure sensor 12 is changed due to a motion of the detection portion of the living body, or when the resistance to the peripheral blood flow is changed due to contraction or expansion of peripheral blood vessels, the values of blood pressure determined based on the radius pulse waves are deflected from the upper-arm blood pressure. Step S16 is provided, for example between steps S9 and S10 of FIG. 5, for detecting an abnormality of the radius pulse waves. In the case of occurrence of a motion of the detection portion of the living body, step S16 is implemented to check whether or not the amplitudes of the radius pulse waves, or the peak values of the same as measured from a reference line (e.g., zero volt line) has been varied more than 50% during unit time (e.g., 5 sec). If the checking at step S16 is found to be affirmative, it means the occurrence of an abnormality of the radius pulse waves. Alternatively, step S16 may be adapted to check whether or not a pulse wave has appeared more than 30% before or after a normal cycle for the radius pulse waves. On the other hand, as shown in FIG. 8, for detecting a change in the resistance to the peripheral blood flow, step S16 is adapted to check whether or not a value indicative of the position of a stepped portion (notch) in the radius pulse wave e.g., length A between the upper peak and the notch / length B between the lower peak and the notch) is varied more than 30% during unit time. The affirmative checking means the occurrence of an abnormality of the pulse waves. Alternatively, step S16 may be adapted to provide an abnormality checking upon detection of a great variation in rate of change (slope) of a portion of the pulse wave corresponding to the diastole of the heart (a down slope C following the notch). In a further alternative, an abnormality of the radial pulse wave is detected by checking whether or not the difference between the leading values of blood pressure determined based on the leading radius pulse wave, which at step S12 has been utilized together with the upper-arm blood pressure H and L to determine a relationship between the radius pulse waves and the upper-arm blood pressure H and L, and the values of blood pressure based on one of the pulse waves following the leading pulse wave, exceeds 40 mmHg, for example.

Figure 9:
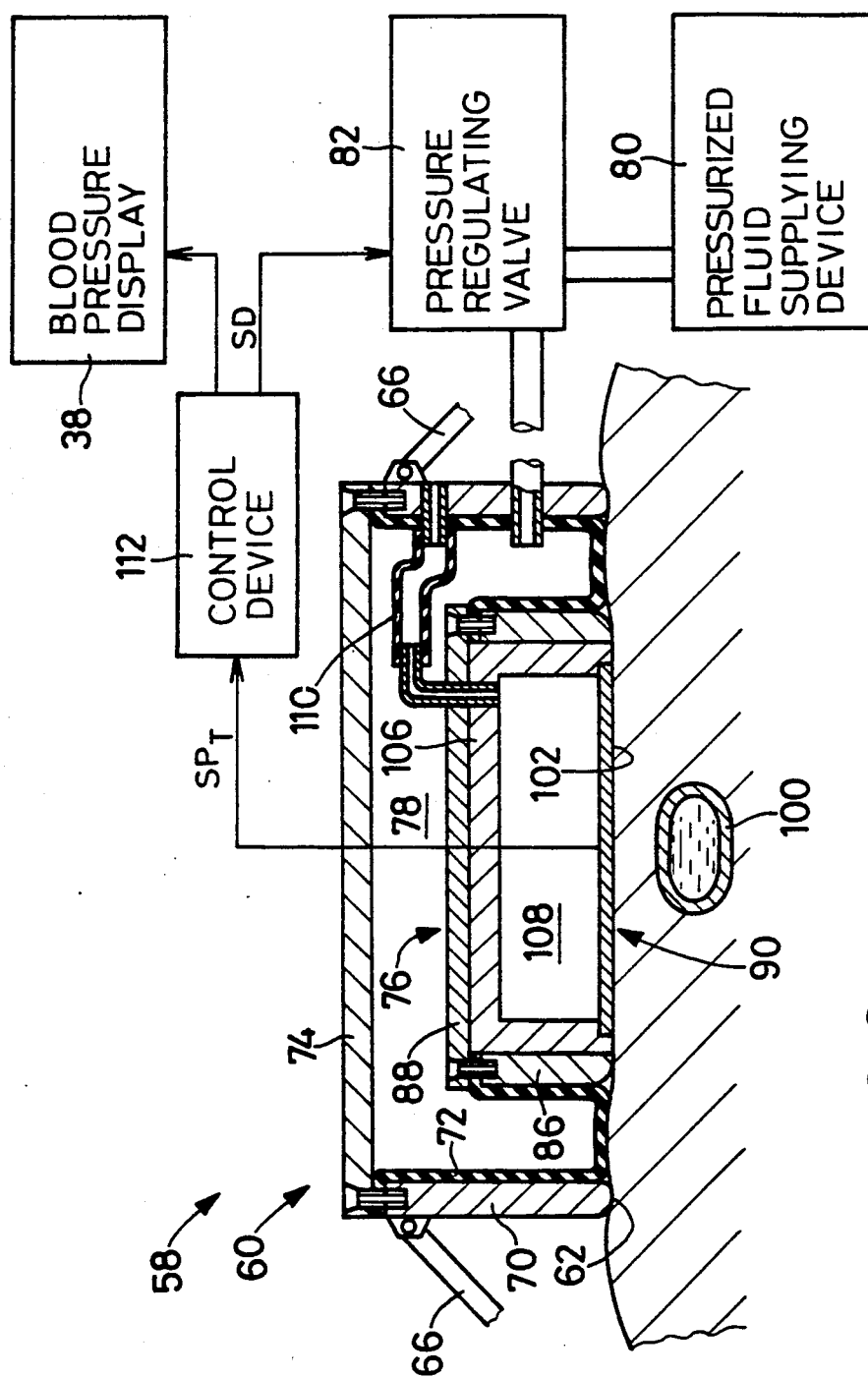
FIG. 9 is a longitudinal cross-sectional view showing the vicinity of a pulse wave sensor of another embodiment of the present invention.

In another embodiment of the present invention, a pulse wave sensor 58 as shown in FIG. 9 is used as the pulse wave detecting means in place of the pulse wave sensor 46 employed in the above described embodiments. In the figure, reference numeral 60 designates a hollow main body which has an opening 62 at its lower end. The main body 60 is removably attached to the living body with the help of a band 66, witt the opening 62 opposed to a body surface of the body above a radius of the living body. The main body 60 consists of an annular side-wall member 70 and a lid member 74 fixed to an upper end of the side wall member 70 with an outer peripheral portion of a diaphragm 72 interposed between the members 70 and 74. An inner peripheral portion of the diaphragm 72 is fixed to a presser member 76. The diaphragm 72 is formed of an elastically deformable material such as rubber, and the presser member 76 is supported by the diaphragm 72 within the main body 60 such that the presser member 76 is movable relative to the main body 60. A pressure room 78 is defined by the main body 60 and the presser member 76. The pressure room 78 is supplied with a pressurized fluid such as a pressurized air, from a pressurized fluid supplying device 80 via a pressure regulating valve 82, whereby the presser member 76 is brought into pressed contact with the body surface of the living body.

The presser member 76 consists of an annular side-wall member 86, a 1-d member 88 fixed to an upper end of the side wall member 86 with the inner peripheral portion of the diaphragm 72 fixed between the members 86, 88, and a presser plate 90 provided in the vicinity of a lower end of the side will member 86. As shown in FIG. 10, the presser plate 90 consists of a semiconductor chip (semiconductor plate) 92 formed of monocrystalline silicon, etc., and a multiplicity of pressure sensitive diodes 94 formed on an upper surface of the chip 92. The diodes 94 are provided with individual terminals 98. A common terminal 96 and each of the terminals 98 cooperate with each other to provide an electrical signal indicative of a variation in pressure of an interface between the corresponding diode 94 and the chip 92. The multiplicity of pressure sensitive diodes 94 are formed on the chip 92 such that, with the main body 60 held on the living body, the diodes 94 are located at regular intervals of distance in a direction substantially perpendicular to a direction of extension of a radial artery 100 whose pulse waves are detected. The width of each diode 94 as viewed in the direction substantially perpendicular to the artery 100 and the above-indicated regular interval of distance are determined such that at least three (seven in the present embodiment) of the diodes 94 are located right above the radial artery 100 and within a length substantially equal to a diameter of the artery 100. The diodes 94 may be formed with an appropriate shape and with an appropriate dimension in a direction parallel to the artery 100.

The presser plate 92 has in a lower surface 102 thereof a multiplicity of recesses at portions corresponding to the multiplicity of diodes 94 provided in the upper surface, each recess being filled with a rubber filler 104. The rubber fillers 104 are provided on the chip 92 such that the fillers 104 do not apply a load to the pressure sensitive diodes 94 and become flush with the lower surface 102. With the pressure sensor 58 held on the body surface of the living body, a portion of the body surface right above, and in the vicinity of, the radial artery 100 is pressed flat under the lower surface 102 of the presser plate 90, and pressure oscillations or pulse waves produced by the artery 100 are transmitted to the diodes 94 through the rubber fillers 104. The portions of the chip 92, at which the recesses to be filled with the fillers 104 are formed, are formed with a remarkably small thickness such as about 15 μm. Where pressure oscillations are transmitted to the rubber fillers 104, the interfaces of the diodes 94 are subjected to a change in pressure, and consequently each diode 94 generates a pulse wave signal $SP_T$, that is an electrical signal indicative of the pressure variation.

The presser plate 90 is fixed to a lower open end of a box-like support member 106 formed of an electrically insulating material and disposed inside the side wall member 86, whereby electrical leakage from the semiconductor chip 92 is prevented. The support member 106 and the presser member 90 cooperate with each other to define a room 108. The room 108 is maintained in communication with atmospheric air through a rubber tube 110, whereby the pressure in the room 108 is not varied due to a body temperature of the living body, etc. Thus, the pulse wave signals $SP_T$ generated by the diodes 94 are free from influence of such a pressure variation.

The pulse wave signals $SP_T$ generated by the pressure sensitive diodes 94 are supplied to a control device 112 via amplifier, band pass filter for selectively passing a frequency component of the pulse waves, and so on (all not shown). The control device 112 is constituted by microcomputer including the A/D converter 50, CPU 28, RAM 34, ROM 32, clock signal generator 56, output interface 36, etc. of the previously described embodiments. As in those embodiments, the control device 112 is adapted to detect pulse waves of the radial artery 100 based on the input pulse wave signals $SP_T$ and command the blood pressure display 38 to display values of blood pressure determined based on the detected pulse waves. The control device 112 also generates a drive signal SD to the pressure regulating valve 82 to regulate the pressure of the pressurized fluid supplied to the pressure room 78.

There will be described the operation of the present embodiment constructed as described above.

Figure 11:
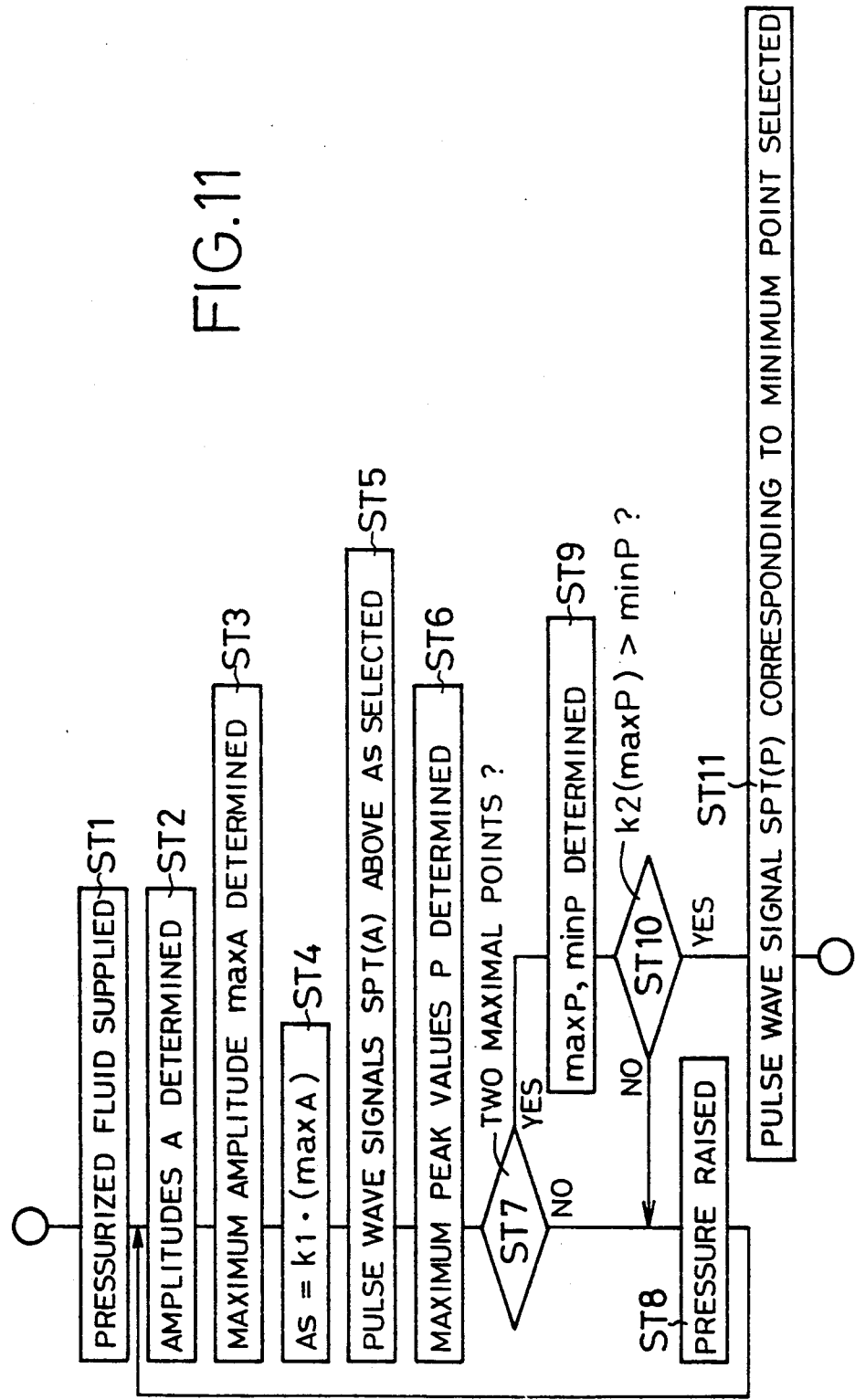
FIG. 11 is a view showing a flow chart used for a portion of the operation of the device of FIG. 9.

With the main body 60 held in the vicinity of a wrist of the living body with the help of the band 66, and with the presser plate 90 of the presser member 76 covering right above the radial artery 100, steps S1 to S7 of the flow chart of FIG. 5 are implemented to measure a maximum and a minimum value of the actual blood pressure of the living body by the cuff 10. Subsequently, the pulse wave detect routine as shown in FIG. 11 is executed in place of steps S8 and S9 of FIG. 5.

To begin with, step ST1 is implemented to generate a drive signal SD for supplying the pressure room 78 with a pressurized fluid with a predetermined constant pressure. Consequently, the presser member 76 is moved relative to the main body 60 toward the body surface of the living body, and eventually the lower surface 102 of the presser plate 90 is brought into pressed contact with the body surface. With the lower surface 102 being in pressed contact with the body surface, pressure oscillations or pulse waves produced by the artery 100 are transmitted to the pressure sensitive diodes 94, which generate pulse wave signals $SP_T$ indicative of the pressure oscillations. The constant pressure, under which the presser plate 76 is pressed on the body surface, is determined at such a degree that the pressure oscillations of the pulse waves can be detected by the diodes 94.

Step ST1 is followed by step ST2 to determine an amplitude A of each of the pulse wave signals $SP_T$ generated by the multiplicity of pressure sensitive diodes 94 arranged in the direction substantially normal to the direction of extension of the artery 100. Subsequently, step ST3 is implemented to determine a maximum amplitude maxA of the thus-determined amplitudes A. Step ST3 is followed by step ST4 to calculate a reference value As by multiplying the maximum amplitude maxA by a predetermined coefficient k1 (1>k1>0), and step ST5 to select pulse wave signals $SP_{T(A)}$ whose amplitudes A are greater than the reference value As. Step ST5 is followed by step ST6 to determine a maximum peak value P of each of the thus-selected pulse wave signals $SP_{T(A)}$. The maximum peak value P, a magnitude of signal, corresponds to a value of blood pressure within the artery 100 at the period of the systole of the heart of the living body. Step ST6 is followed by step ST7 to check whether or not a varying trend of the maximum peak values P of the pulse wave signals $SP_{T(A)}$ in the direction intersecting the artery 100 has a pair of maximal points.

Steps ST2 through ST5, above indicated, are provided for selecting the pulse wave signals generated by the pressure sensitive diodes 94 positioned in the vicinity of a portion of the body surface right above the artery 100. More specifically, as shown in FIG. 12, the amplitudes A of the pulse wave signals $SP_T$ generated by the diodes 94 located right above the artery 100 are greater than those of the signals generated by the other diodes 94, as viewed in the direction normal to the artery 100. In the case where the presser member 76 is pressed on the body surface such that the artery 10f becomes generally depressed under the pressure exerted by the presser member 76, nine pulse wave signals $SP_T$ from the nine diodes 94 located in the vicinity of the portion of the body surface right above the artery 100, are selected as the signals $SP_{T(A)}$, as shown by the graph (c) in FIG. 12. The coefficient k1 employed for calculation of the reference value As is pre-determined so that the pulse wave signals $SP_T$ generated by the pressure sensitive diodes 94 in the vicinity of the portion of the body surface right above the artery 100 can be selected as the signals $SP_{T(A)}$.

Figure 13A:
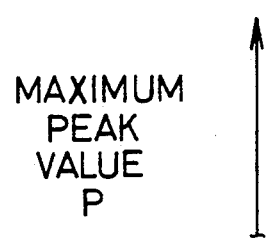
FIG. 13 is a view of three graphs each showing maximum peak values of the pulse wave signals generated by the pressure sensors in the direction perpendicular to the arterial vessel, the pressing forces used in the three cases being different from each other.
Figure 13B:
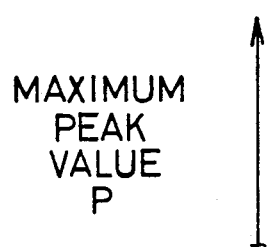
Figure 13C:
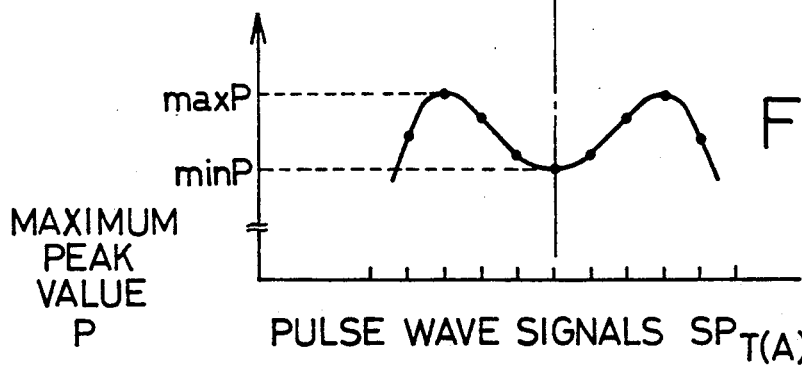

The graph (c) of FIG. 13 illustrates a varying trend of the maximum peak values P of the selected pulse wave signals $SP_{T(A)}$ in the direction intersecting artery 100. Likely, the graph has a minimal point at a position corresponding to a generally middle point of the portion of the body surface right above the artery 100 and a pair of maximal points at the opposite ends of the portion of the body surface right above the artery 100. In such a case, the checking at step ST7 is found to be affirmative. The reason of this is that, since with the artery 100 assuming a generally depressed shape a portion of the wall of the artery 100 corresponding to around the middle point of the portion of the body surface right above the artery 100 is in parallel relationship with the presser plate 90, pressure oscillations or pulse waves transmitted perpendicularly to the parallel portion of the artery wall are almost free from influence of tension of the wall, on the other hand the diodes 94 positioned in the vicinity of the opposite ends of the portion of the body surface right above the artery 100 detect a relatively high pressure since pressure oscillations transmitted to curved portions of the artery wall located on both sides of the parallel portion thereof and corresponding to the above-indicated opposite ends, are influenced by the tension of the artery wall.

However, at present, when the pressure of the pressurized air supplied to the pressure room 78 is relatively low, the pressing force under which the presser member 76 is pressed on the body surface of the living body is small, and accordingly the artery 100 does not assume the depressed shape. The graph (a) of FIG. 12 shows this condition, that is, a varying trend of the amplitudes A of the pulse wave signals $SP_T$, which has a maximal point in the vicinity of the middle point of the portion of the body surface right above the artery 100. Consequently, at step ST5, one or several pulse wave signals $SP_T$ in the vicinity of the middle point are selected as the signals $SP_{T(A)}$. The graph (a) of FIG. 13 shows a varying trend of the maximum peak values P of the thus-selected pulse wave signals $SP_{T(A)}$. Since the artery 100 has not been depressed yet, the graph has a sole maximal point in the vicinity of the middle. Accordingly, the checking at step ST7 is found to be negative, and step ST7 is followed by step ST8.

Step ST8 is provided to generate a drive signal SD to the pressure regulating valve 82 to raise the pressure of the pressurized fluid supplied to the pressure room 78 by a predetermined increment. Step ST8 is followed by steps ST2 and the following to determine another reference value As based on pulse wave signals $SP_T$ newly generated by the multiplicity of pressure sensitive diodes 94, select pulse wave signals $SP_{T(A)}$ whose amplitudes A are above the newly determined reference value As, and check whether or not a graph of maximum peak values P of the thus-selected signals $SP_{T(A)}$ has a pair of maximal points. As the pressure of the pressurized fluid supplied to the pressure room 78 is gradually raised at step ST8, the pressing force under which the presser member 76 is pressed on the body surface is raised correspondingly. Accordingly, as the implementation of step ST8 is repeated, the artery 100 is gradually depressed and consequently the varying trend of the amplitudes A of the pulse wave signals $SP_T$ comes to assume a curve of the graph (b) of FIG. 12. Also, the varying trend of the maximum peak values P of the pulse wave signals $SP_{T(A)}$ selected at step ST5 assumes a curve of the graph (b) of FIG. 13. When the varying trend of the maximum peak values P of the signals $SP_{T(A)}$ comes to have a pair of maximal points as shown in the graph (c) of FIG. 13, the checking at step S7 is found to be affirmative, and step ST7 is followed by step ST9.

Step ST9 is provided to determine a maximum value maxP and a minimum value minP. The maximum value maxP is defined as an average value of the maximum peak values P of the above-indicated pair of maximal points, and the minimum value minP is defined as a maximum peak value P of the above-indicated minimal point located between the pair of maximal points. Step ST9 is followed by step ST10 to check whether or not the minimum value minP is smaller than a value obtained by multiplying the maximum value maxP by a predetermined coefficient k2 ($1 > k2 > 0$). Step ST10 is provided for seeing whether or not the artery 100 has been depressed to such an extent that the pressure oscillations or pulse waves detected by the diodes 94 in the vicinity of the middle of the portion of the body surface right above the artery 100 are almost free from influence of tension of the wall of the artery 100. The coefficient k2 is empirically pre-determined taking account of elasticity of the artery 100. The implementation of steps ST8, ST2 and the following are repeated to raise the pressure of the pressurized fluid supplied to the pressure room 78 until the checking at step ST10 is found to be affirmative.

Once the checking at step S10 is found to be affirmative, step ST10 -s followed by step ST11 to select the pulse wave signal $SP_{T(A)}$ having the minimum value minP, as a pulse wave signal $SP_{T(P)}$. The thus-selected pulse wave signal $SP_{T(P)}$ is continuously detected and stored. The pulse waves represented by the signal $SP_{T(P)}$ with the minimum value minP are almost free from the influence of tension of the artery wall, as previously stated, and have a good approximation in absolute value to actual pulse waves (pressure waves) transmitted through the artery 100. Step ST11 is followed by steps S10 and the following, as in the previously described embodiments, to determine a maximum and a minimum value of each of the pulse waves represented by the signal $SP_{T(A)}$ and update the correspondence relationship between the pulse waves and the actual blood pressure at the predetermined interval of time by utilizing the measurements of the actual blood pressure which are obtained at the predetermined interval.

Accordingly, in the present embodiment, as in the previously described embodiments, it is not necessary to always press a portion of the living body under a comparatively high pressure to continuously monitor blood pressure of the living body. As a result, the living body whose blood pressure is monitored during a long period of time is free from blood congestion or appreciable discomfort. Furthermore, the thus-obtained values of blood pressure are accurate since they are almost free from influence of breathing, and are continuous, that is, one blood pressure for each pulsation of the arterial vessel.

In the present embodiment, the pressing force under which the pressure sensitive diodes 94 are pressed on the body surface is regulated so that the maximum peak value P of the pulse wave signal $SP_T$ from the middle of a group of the diodes 94 which group is located on the portion of the body surface right above the artery 100 is lower than those of the signals $SP_T$ from the diodes 94 positioned at the opposite ends of the group, that is, that the artery 100 becomes generally depressed. Thus, the pressure sensitive diodes 94 are pressed on the living body under a most appropriate pressure, irrespective of individualities of the living bodies to be monitored, and the accuracy of detection of the pulse waves are increased.

While the preferred embodiments of the present invention have been described with reference to the drawings, the present invention may be otherwise embodied.

For example, while in the previously described three embodiments the pulse wave sensor 46, 58 is adapted to be located above the radius, the pulse wave sensor 46, 58 may be held above a carotoid artery, a dorsal pedal artery, or on other sites on the skin of the living body right below which an arterial vessel extends and therefore at which pulse waves are easily detected.

While in the embodiment of FIG. 2 the pulse wave sensor 46 is pressed under a predetermined low pressure against the arterial vessel above the radius with the band 52 wound around the wrist of the living body, the pulse sensor 46 may be adapted to be fixed to an inside of a cuff, similar to the cuff 10, which is wound around a site at which pulse waves are detectable. In this case, the cuff is inflated under a comparatively low, constant pressure, for example not more than about 20 mmHg, so that the pulse wave sensor 6 is pressed against the arterial vessel above the radius under the constant low pressure.

While the previously described three embodiments are adapted to utilize the peak values (maximum values) of the pulse waves for determining the maximum values of blood pressure SYS, it is possible to utilize a speed of increase of each pulse wave, that is a time lapse from a lower peak to an upper peak of each pulse wave, or a slope (rate of change) of an increasing portion of the same, for determining a maximum value SYS. It is known that the steeper an increasing portion of a pulse wave is the higher a maximum blood pressure is.

While in the above described embodiments the actual blood pressure of the living body is measured at regular intervals of time during the monitoring of blood pressure for the purpose of updating the relationship between the actual blood pressure and the pulse waves at the regular intervals it is possible to obtain one measurement of the actual blood pressure and one pulse wave to determine a relationship therebetween, before starting the monitoring, and utilize the thus-determined relationship, without updating it, throughout the monitoring.

In the previously described three embodiments, the correspondence relationship between the values of actual blood pressure and the magnitudes of pulse waves is determined on the assumption that the values of actual blood pressure is in proportion to the magnitudes of pulse waves. However, such a correspondence relationship may be obtained in the form of a quadratic function, in which the values of blood pressure are expressed as a quadratic function of the magnitudes of pulse waves. Alternatively, the correspondence relationship may be determined by selecting, from a plurality of pre-programed data maps representing different correspondence relationships between the values of blood pressure and the magnitudes of pulse waves, one data map corresponding to the values of blood pressure, and the magnitudes of pulse wave, of the subject being monitored.

While in the previous three embodiments the actual blood pressure of the living body is measured at step S6 by the so-called "oscillometric method" in which the blood pressure is determined based on magnitudes of pulse waves and in the course of deflation of the cuff 10, it is possible to measure the actual blood pressure by the microphone method in which a microphone is employed to detect Korotkoff sound and the blood pressure is determined based on presence or absence of the Korotkoff sound, or by a method in which supersonic wave is utilized for detecting wave motions of the wall of an arterial vessel and the blood pressure is determined based on a change in magnitude of the wave motions. Alternatively, the actual blood pressure may be measured in the course of inflation of the cuff 10.

Furthermore, while in the illustrated three embodiments the successively determined maximum and minimum values of blood pressure are displayed on the Braun tube, it is possible to concurrently record the values of blood pressure on a chart or other sorts of recording or printing sheets. Moreover, in place of those displaying or recording means, a variety of other displaying or recording means may be employed.

It is to be understood that the foregoing descriptions are provided for illustrating the preferred embodiments of the present invention and that the present invention may be modified with various changes without departing from the spirit and scope thereof.

We claim:

1. A blood pressure monitoring system for continuously measuring blood pressure of a living body, the system comprising:

pulse wave detecting means for detecting pulse waves of an arterial vessel of said living body, said pulse wave detecting means comprising a plurality of pressure sensors which are adapted to be set on a body surface of said living body above said arterial vessel, each of said pressure sensors having a dimension smaller than a diameter of said arterial vessel as viewed in a direction perpendicular to said arterial vessel;

pressing means for pressing said pulse wave detecting means against said arterial vessel via said body surface and thereby at least partially flattening said arterial vessel, at least one of said pressure sensors detecting said pulse waves through a flattened wall of said arterial vessel;

blood pressure measuring means for measuring an actual blood pressure of said living body;

control means for determining a relationship between blood pressure and magnitude of pulse waves, based on the pulse waves detected by said at least one pressure sensor through said flattened wall of said arterial vessel and the actual blood pressure measured by said blood pressure measuring means, such that blood pressure is a linear function of magnitude of said pulse waves, said control means determining blood pressures according to the thus-determined relationship based on magnitudes of the pulse waves detected by said at least one pressure sensor through said flattened wall of said arterial vessel; and display means for displaying the blood pressures determined by said control means.

2. A blood pressure monitoring system as recited in claim 1, wherein said pulse wave detecting means is adapted to be located on the body surface of said living body above a radial artery, a carotid artery, or a dorsal pedal artery of said living body.

3. A blood pressure monitoring system as recited in claim 1, wherein said pulse wave detecting means comprises a semiconductor strain sensor or a piezoelectric element.

4. A blood pressure monitoring system as recited in claim 1, wherein said pulse wave detecting means is pressed against said arterial vessel of said living body via said body surface under a predetermined pressure by said pressing means.

5. A blood pressure monitoring system as recited in claim 4, wherein said pressure applied to said pulse wave detecting means is predetermined to be a comparatively low, constant pressure not more than about 20 mmHg.

6. A blood pressure monitoring system as recited in claim 4, wherein said pressing means comprises a band which is wound around a body portion of said living body.

7. A blood pressure monitoring system as recited in claim 1, wherein said pressure sensors of said pulse wave detecting means are arranged in a direction intersecting said arterial vessel on the body surface of said living body above said arterial vessel, each of said pressure sensors being pressed on said body surface and generating a pulse wave signal representative of said pulse waves produced by said arterial vessel, the system further comprising pressure force regulating means for regulating a pressing force of said pressing means so that a magnitude of the pulse wave signal from the middle of a group of said plurality of pressure sensors which group is located on a portion of said body surface right above said arterial vessel, is lower than magnitudes of the pulse wave signals from the opposite ends of said group.

8. A blood pressure monitoring system as recited in claim 7, wherein said plurality of pressure sensors comprise a single semiconductor plate and a plurality of pressure-sensitive diodes formed on said single semiconductor plate, said semiconductor plate being pressed against said arterial vessel via said body surface by said pressing means so as to at least partially flatten said arterial vessel, each of said plurality of pressure-sensitive diodes having said dimension smaller than said diameter of said arterial vessel.

9. A blood pressure monitoring system as recited in claim 7, wherein said pressing means comprises a main body, a presser member provided inside said main body, an elastically deformable diaphragm which is disposed between said presser member and said main body to air-tightly define a pressure room and support said presser member such that said presser member is movable relative to said main body, and a pressurized fluid supplying means for supplying a pressurized fluid to said pressure room.

10. A blood pressure monitoring system as recited in claim 7, wherein said pressing force regulating means determines maximum peak values of said pulse wave signals generated by said plurality of pressure sensors and regulates said pressing force of said pressing means so that a varying trend of said maximum peak values in the direction intersecting said arterial vessel has a pair of maximal points and a minimal point located between said pair of maximal points and that the maximum peak value of said minimal point is not more than a predetermined proportion of an average of the maximum peak values of said maximal points.

11. A blood pressure monitoring system as recited in claim 1, wherein said control means determines a maximum blood pressure based on a speed of increase of the pulse wave or a rate of change of an increasing portion of the pulse wave.

12. A blood pressure monitoring system as recited in claim 1, wherein said control means determines said relationship by selecting, from a plurality of pre-stored data maps representing different relationships between blood pressure and magnitude pulse waves, one data map corresponding to a relationship between the actual blood pressure measured by the blood pressure measuring means and the pulse waves detected by the pulse wave detecting means.

13. A blood pressure monitoring system as recited in claim 1, wherein said control means stores said relationship, and calculates blood pressures according to the stored relationship based on magnitudes of the pulse waves detected after said relationship has been stored.

14. A blood pressure monitoring system as recited in claim 1, wherein said control means updates said relationship at predetermined regular intervals of time based on the actual blood pressures which are measured by said blood pressure measuring means at said predetermined regulate intervals.

15. A blood pressure monitoring system as recited in claim 14, wherein the regular interval of time is predetermined to fall within the range of about 5 to 10 minutes.

16. A blood pressure monitoring system as recited in claim 1, wherein said control means includes abnormal pulse wave detecting means for detecting an abnormality of the pulse waves, said blood pressure measuring means automatically measuring an actual blood pressure of said living body upon the detection of said abnormality of the pulse waves, said control means updating said relationship based on the thus-measured actual blood pressure and the pulse waves detected after the detection of said abnormality.

17. A blood pressure monitoring system as recited in claim 1, wherein said blood pressure measuring means includes a cuff which is wound around a body portion of said living body, and a pressure supplying means for supplying a pressure to said cuff, said blood pressure measuring means determining said actual blood pressure based on variation in magnitude of the pulse waves of said arterial vessel which variation is detected through said cuff as the pressure of said cuff is varied.

18. A blood pressure monitoring system as recited in claim 1, wherein said blood pressure measuring means measures actual maximum and minimum blood pressures of said living body, said control means determining a maximum and a minimum magnitude of one of the pulse waves detected by said pulse wave detecting means, and determining a first relationship between maximum blood pressure and maximum pulse wave magnitude and a second relationship between minimum blood pressure and minimum pulse wave magnitude, said first and second relationships being expressed by linear functions (1) and (2), respectively, $$SYS = Kmax \cdot Mmax$$

$$DIA = Kmin \cdot Mmin$$

wherein
SYS is maximum blood pressure,
Kmax is a constant,
Mmax is maximum pulse wave magnitude,
DIA is minimum blood pressure,
Kmin is a constant, and
Mmin is minimum pulse wave magnitude,
said control means determining said constants Kmax, Kmin by dividing the actual maximum and minimum blood pressures measured by said blood pressure measuring means, by the maximum and minimum pulse wave magnitudes determined thereby, respectively, said control means determining a maximum and a minimum blood pressure of said living body according to said linear functions (1), (2) based on a maximum and a minimum magnitude of each of the pulse waves detected by said pulse wave detecting means after said linear functions (1) and (2) have been determined.

* * * * *